United States Patent [19]
Hradil et al.

[11] 3,964,973
[45] June 22, 1976

[54] PREPARATION OF INSOLUBLE BIOLOGICALLY ACTIVE COMPOUNDS

[75] Inventors: Jiří Hradil; Jiří Čoupek; Miroslava Křiváková; Jiří Štamberg; Arthur Stoy, all of Prague; Jaroslava Turková, Cesky Brod, all of Czechoslovakia

[73] Assignee: Ceskoslovenska akademie ved, Prague, Czechoslovakia

[22] Filed: Jan. 30, 1974

[21] Appl. No.: 438,011

[30] Foreign Application Priority Data
Feb. 5, 1973    Czechoslovakia .................... 842-73

[52] U.S. Cl. .................................. 195/68; 195/63; 195/DIG. 11; 260/112 R; 424/94
[51] Int. Cl.² ........................................ C07G 7/02
[58] Field of Search ................. 195/63, 68, DIG. 4; 260/112 R; 424/94

[56] References Cited
UNITED STATES PATENTS

| 3,645,852 | 2/1972 | Axen et al. ....................... 195/63 X |
| 3,711,574 | 1/1973 | Jeworek et al. ................... 195/63 X |
| 3,764,477 | 10/1973 | Lehmann et al. ..................... 195/63 |
| 3,821,083 | 6/1974 | Leemputten et al. ..... 195/DIG. 11 X |

Primary Examiner—David M. Naff
Attorney, Agent, or Firm—Murray Schaffer

[57] ABSTRACT

Biologically active compounds such as enzymes are insolubilized by hydrophilizing a macroporous substantially hydrophobic carrier by hydrolysis of a thin surface layer of the carrier to form free carboxylic acid groups, and thereafter activating the carrier and reacting the activated carrier with a biologically active compound.

5 Claims, No Drawings

PREPARATION OF INSOLUBLE BIOLOGICALLY ACTIVE COMPOUNDS

The invention relates to a method for preparation of insoluble biologically active compounds.

A porous glass, cellulose and its derivatives, starch, polystyrene derivatives, copolymers of maleic anhydride with ethylene, polyacrylamide and polysaccharides have been used for insolubilization of biologically active compounds such as enzymes, coenzymes, enzyme inhibitors, hormones, antigens, immuneactive compounds, and the like. The low mechanical strength, low hydrolytic stability and hydrophobity of the carrier surface are shortcomings of most the these materials.

The low mechanical strength prevents operation under pressure, which is a condition for higher flow rates through the gel column. Besides polysaccharides, also biologically active compounds encapsulated into a lightly crosslinked three-dimensional network of polymer have low mechanical strength. In addition, the three-dimensional network often very strongly influences the biological activity of encapsulated compounds due to diffusion process. The low hydrolytic stability, e.g. of polysaccharides, is not desired in the case of enzyme insolubilization. Such cases are also known, where the reaction of a substrate with a biologically active compound bound to a carrier is complicated by the insufficient hydrophility of the carrier surfce (e.g. polystyrene), or by non-specific sorption at its surface.

Advantages of the immobilized biologically active compounds may be shown for example for insoluble enzymes. The annual world production of enzymes used in the pharmaceutical and food industry for catalysis of chemical reactions ranges over thousands of metric tons. Difficulties in their preparation, a relatively high price, low stability, and particularly the uneconomical way of application prevents their broader use in the industrial scale. This is because the recent procedures do not permit recovery of the enzymes once used.

The enzyme recovery and repeated use either in a batch or in a through-flow process is enabled by linking the soluble enzyme to the polymeric carrier.

The invention consists in formation of active anhydride groups in the polymeric carrier, which are able to bind biologically active compounds, but only in a thin surface layer of the macroporous polymer or copolymer carrier which is substantially hydrophobic, by a surface hydrolysis and the further activating processing which is followed by reaction of the carrier with the biologically active compound. The above mentioned activation processing consists in transformation of free caboxylic groups into anhydride groups by heating under reduced pressure or by action of dehydrating agents.

According to the present invention, insoluble biologically active compounds such as e.g. enzymes which are proteins, coenzymes, enzyme inhibitors, antidotes, hormones, immuneactive compounds, antibiotics, etc., can be prepared by binding them to superficially hydroplilized, substantially hydrophobic and non-swelling macroporous polymers and copolymers based, for instance, on alkylene diacrylates, alkylene dimethacrylates, oligo- and polyglycol acrylates, oligo- and polyglycol methacrylates, alkylenediacrylamides, hydroxyalkyl acrylates, hydroxyalkyl methacrylates, oligo- and polyglycol monoacrylates, oligo- and polyglycol monomethacrylates, acrylonitrile, methacrylonitrile, which monomers can be replaced in part by vinyl monomers such as vinylaniline, vinylpyridine, vinylcarbazole, etc. Such macroporous copolymers are superficially hydrophilized by means of a partial hydrolysis and activated either by known compounds which react with a hydroxyl, amine or caboxylic group, e.g. by cyanogen bromide, anhydride or chloride of carboxylic acid, diisocyanate or isothiocyanate, or by transformation of adjoining caboxylic groups into anhydride groups and the resulting hydrophilized and activated gels are subjected to reaction with soluble biologically active compounds which effects their insolubilization through covalent bonding, while the total activity is retained. The hydrolysis is carried out in an acidic or alkaline medium. If it is run in the alkaline medium, 2 to 10 M sodium hydroxide is preferably used at the temperature 60° – 135°C for 30 to 120 min.

The present invention relates above all to the polymers with anhydride reactive groups, without limiting the scope of it. Carboxylic acid anhydrides are important acylating agents in the organic chemistry of low-molecular-weight compounds and find their aplication e.g. in reactions with hydroxyl or thiol groups. The transformation into anhydride may consist in heating of the hydrophilized polymers or copolymers to the temperatures 200° to 250°C for 30 to 300 minutes at the pressure 0.2 to 0.01 Torr.

Macromolecular analogues of these reactions were studied to much less extent (Goodrich Co., inventor R. M. Summers: U.S. Pat. No. 2,967,175 (1958); Monsanto Chemical Co.: Brit Pat. No. 815,821 (1958); Monsanto Chemical Co., inventor R. M. Hedrick, J. A. Herbig: Ger. Pat. No. 1,109,373 (1956) ). All works published till now used only polymeric anhydrides which were prepared from corresponding monomers, namely from maleic anhydride, acrylic or methacrylic anhydrides. A high concentration of polymeric anhydrides may be prepared according to the invention in the hydrophilized superficial layer of current polymers, namely of polymers based on esters or nitriles of polyacrylic and polymethacrylic acid, while the good mechanical properties of the starting hydrophobic polymers with hydrophilized surface and reactive groups enable not only successful bonding of the biologically active compounds, but also their easy and effective application.

Highly cross-linked polymers are best suited for the procedure according to the invention. However, some completely non-swelling polymers such as polyacrylonitrile or poly(methyl methacrylate), may be used also in non-crosslinked or only lightly crosslinked state. The crosslinking is achieved not only by addition of cross-linking agents, but also by a chain transfer, especially for acrylonitrile.

The polymers containing various concentrations of anhydride groups can be prepared by the simple procedure according to the invention. For instance, polymeric esters or nitriles are hydrolyzed up to the required degree by action of 2 – 9 M NaOH for 0.5 – 2 hours at the temperature 80° – 130°C. It is known, that this reaction proceeds in microblocks, advantageously in regions with the isotactic structure. The places with a clean-cut ability to close the prefered six membered anhydride cycles are formed in the surfce hydrophilized layer in this way. This cannot be attained by copolymerization of the monomeric acid, because the occurence of carboxylic groups in the chains would be random and the probability of formation of the cyclic anhydrides would be suppressed. According to the proposed procedure, the partial alkaline hydrolysis is followed by an acidic treatment, to transform carboxylic groups into the $H^+$ form, and eventually by anhydride formation through thermic dehydration at the temperature 200° – 250°C and the pressure below 0.1 Torr or by treatment with known dehydrating agents such as e.g. acetanhydride at 20° to 140°C or thionyl chloride at −10 to +20°C. Both reactions last mentioned may be advantageously catalyzed by pyridine or other acidobasic catalysts. The reactive anhydride groups formed can be proved by the infrared spectra (bands at 1785 and 1050 $cm^{-1}$).

EXAMPLE 1

A low-hydrophilic macroporous gel (2.5 parts) consisting of 90 wt.% of ethylene dimethacrylate and 10 wt.% of 2-hydroxyethyl methacrylate and having the specific surface area 209 $m^2/g$, was hydrophilized by heating with 10 parts of 9 M NaOH to the temperature 125°C for 1 hour. The superficially hydrolyzed gel thus prepared was filtered, transformed into the $H^+$ form with 200 parts of 2 M HCl, thoroughly washed with water and dried in a vacuum oven. Reactive anhydride groups were formed by heating of the superficially hydrophilized copolymer to the temperature 230°C for 4 hours under the pressure 0.1 Torr. The dehydrated gel was swollen in 75 parts of 2 M phosphoric buffer solution of pH 7.5, the mixture was cooled and added under stirring into a solution of 1 part of chymotrypsin in 25 parts of 2 M phosphate buffer solution. The reaction mixture was stirred and cooled with ice to 4°C for 24 hours. The gel with chemically bound enzyme was then sucked off, washed with the buffer solution and water, and activated by washing with 400 parts of 0.1 M solution of sodium borate and 1 M sodium chloride (pH 8.5), further by 300 parts of 0.1 M sodium acetate (pH 4.1) and 300 parts of 0.01 M sodium acetate (pH 4.1). The concentration of the insolubilized enzyme prepared in this way was 3 mg related to 1 ml of the gel. The bound enzyme exhibited the esterase and proteolytic activities.

EXAMPLE 2

A hydrophilic macroporous poly(ethylene diacrylate) 2,4 parts of the grain size 0.1 – 0.2 mm, was swollen in 10 parts of 9 M NaOH and hydrolyzed by heating to the temperature 130°C for 0.5 hours. Then it was transformed into the $H^+$ form and dehydrated by heating to 225°C for 4 hours at the pressure 0.1 Torr. Chymotrypsin was linked to the gel by procedure described in EXAMPLE 1 in the amount 1.5 mg per 1 ml of the gel.

EXAMPLE 3

A low-hydrophilic macroporous copolymer (2.5 wt. parts) of ethylene dimethacrylate with 50 wt.% of 2-hydroxyethyl methacrylate, having a specific surface area 97.2 $m^2/g$, was hydrolyzed with 9 M NaOH for 2 hours at the temperature 125°C. The gel was transformed into the $H^+$ form and the surface anhydride layer was formed by heating to the temperature 200°C at the pressure 0.05 Torr for 4 hours. Chymotrypsin was linked to the activated gel in the amount of 7.6 mg of the active enzyme per one mililiter of the gel, by the procedure described in Example 1.

EXAMPLE 4

The diethylene glycol methacrylate gel containing 50 wt.% of diethylene glycol dimethacrylate (2.5 wt. parts) was hydrolyzed by 10 parts of 9 M NaOH at 80°C for 2 hours. After this reaction, the gel was filtered off, transformed into the $H^+$ form by 200 parts of 2 M HCl, washed with water and dried at 78°C and 0.05 Torr. The superficially hydrolyzed gel was dispersed in 200 parts of diethyl ether containing 2.5 parts of pyridine. Acetanhydride (2.5 parts) in 10 parts of diethyl ether as added to the dispersion and stirred for 4 hours at the ambient temperature. The gel was then sucked off on a sintered glass filter, washed with 100 parts of ice water and 10 parts of ethanol, sucked off and dried in vacuo or used immediately for further conversions described in EXAMPLE 1.

EXAMPLE 5

A macroporous copolymer (2.5 wt. parts), prepared from ethylene diacrylate with 50 % of 2-hydroxyethyl methacrylate was hydrolyzed as in EXAMPLE 1 and the superficially hydrolyzed gel was, after washing and drying without further chemical treatments, heated under a reflux condenser with 5 parts of acetanhydride to the temperature 118° – 140°C. After the reaction, the suspension was cooled to 0°C, filtered and the gel was washed with 100 parts of ice water and ethanol, and dried in vacuo. The gel activated in this way was swollen in 75 parts of the phosphate buffer solution (pH 7.5) and the mixture was cooled and added to a solution of 1 part of trypsin in 25 parts of the buffer solution under stirring. The mixture was stirred at 4°C for 24 hours and then lyophilized as described in EXAMPLE 1.

EXAMPLE 6

A hydrophilic macroporous gel (2.5 wt. parts), consisting of 75 wt.% of ethylene dimethacrylate and 25 wt.% of 2-hydroxyethyl methacrylate and having the specific surface area 159.7 $m^2/g$, was swollen in 10 parts of 9 M NaOH and superficially hydrolyzed for 2 hours and the temperature 100°C. The gel was then thoroughly washed with water and dried to the constant weight. The converted gel was dispersed in 20 parts of diethyl ether. The suspension was cooled to −10°C and a solution of 0.5 parts of thionyl chloride in 5 parts of diethyl ether was dropwise added under stirring. Sodium chloride precipitated after addition of the thionyl chloride solution immediately. The gel was tirred at −10°C another hour, sucked off on a sintered glass filter, washed with 100 parts of ice water and 10 parts of ethanol, sucked off and dried in vacuo or used without further operation to conversions described in EXAMPLE 1.

EXAMPLE 7

A low-hydrophilic macroporous gel (2.5 wt. parts) prepared by copolymerization of ethylene dimethacrylate with 10 wt.% of 2-hydroxyethyl methacrylate was hydrophilized by heating with 10 parts of 9 M NaOH to the temperature 125°C for 1 hour. The hydrophilized gel prepared in this way was filtered, transformed into the $H^+$ form by 200 parts of 2 M HCl, and thoroughly washed with water. The gel was then stirred into 10 parts of distilled water and 10 parts of 10% aqueous cyanogen bromide, prepared shortly before use, were added dropwise into the suspension under continuous stirring. After the cyanogen bromide solution was added, the suspension was adjusted to pH 11 by 4 M NaOH and this pH was maintained for 12 minutes by further additions of 4 M NaOH under continuous stirring at the ambient temperature. This suspension was then filtered as rapidly as possible and washed with 200 parts of ice-cold 0.1 M NaHCO$_3$ on the sintered glass filter. The gel was sucked off, dispersed in 10 ml of 0.1 M NaHCO$_3$ and stirred after addition of 1 g of solid chymotrypsin for 24 hours at 4°C. The gel with the chemically bound enzyme was then sucked off and activated by washing with 400 parts of 0.1 M sodium borate - 1 M sodium chloride solution (pH 4.1), 300 parts of 0.1 M sodium acetate - 1 M sodium chloride (pH 4.1) and 300 parts of 0.1 M sodium acetate (pH 4.1). The enzymes insolubilized in this way exhibited both esterase and proteolytic activities.

EXAMPLE 8

A hydrophilic macroporous poly(methyl methacrylate -co- ethylene dimethacrylate) (12.4 wt. parts), having the grain size 100 – 200 μm, was superficially hydrophilized, activated and used for the chymotrypsin insolubilization according to EXAMPLE 1. The concentration of the bound enzyme was 1.4 mg per ml of the enzyme.

EXAMPLE 9

A microporous hydrophobic copolymer consisting of 50 wt.% of acrylonitrile and 50 wt.% of ethylene dimethacrylate was hydrophilized and activated as described in EXAMPLE 1 and used for the enzyme immobilization.

EXAMPLE 10

A mixture of 53 wt. parts of acrylonitrile and 47 parts of 65 % colorless nitric acid was initiated with 0.1 g of ammonium peroxodisulfate, 0.3 g of dimethylaminoethyl acetate and 0.005 g of silver nitrate, where peroxodisulfate and silver nitrate were used as 10% aqueous solutions. The polymerization proceeded in a glass cylinder under exclusion of oxygen access at 15°C for 5 days and the solution was transformed into a white mass, which was readily removeable from the cylinder due to contraction during polymerization. The cylinder of porous polyacrylonitrile was washed first by tap water for 1 day and then in several times changed 1% aqueous sodium bicarbonate solution for 1 day in such a way, that the washing liquid was sucked through the cylinder closely surrounded with a polyethylene jacket. Then, the alkaline hydrolysis was carried out by sucking 6 M aqueous sodium hydroxide 90°C warm through the porous column, followed by suction of distilled water through to the neutral reaction. The column was then dried by passing the warm air, cooled, washed with cold diethyl ether (at −10°C), and soaked by suction with cold 10% etherous thionyl chloride solution under cooling to −10°C, to form active anhydride groups. Ether was then sucked off and distilled water was sucked through the column to the neutral reaction. The column can be used in this state for fixing biologically active compounds by the procedure described in the preceding examples.

EXAMPLE 11

A mixture consisting of 30 parts of acrylonitrile, 20 parts of methyl methacrylate, 10 parts of divinylbenzene and 40 parts of toluene was initiated with 0.2 parts of azobisisobutyronitrile and suspension copolymerized in the saturated sodium chloride solution at 75°C.

The suspension was separated after 8 hours, washed with ether, dried and packed into a column, through which 100°C warm 5 M sodium hydroxide was circulated in a closed circuit for 1 hour. The polymer was then washed by distilled water into the neutral reaction in the column, dried by sucking a warm air through, washed with cold ether and thionyl chloride solution and further worked out according to EXAMPLE 10.

The thickness of the hydrolyzed layer at the surface of hydrophobic polymer depends both on the concentration of a hydrolizing agent, and the temperature and duration of treatment. These conditions may be therefore arbitrarily varied according to known principles, e.g. in such a way that a higher temperature is used at the lower agent concentration or a shorter treatment at the higher temperature. The invention is by no means limited to the conditions given in examples. The acid hydrolysis can be also used, indeed, besides the alkaline hydrolysis, using a strong mineral acid as sulfuric or hydrochloric acid. The transormation of the polymer into the H$^+$ form is then omitted. However, the more diluted acid and higher temperature have to be used for hydrolysis of nitrile groups, otherwise amide groups are pedominantly formed. Therefore, the acid hydrolysis is more suitable for polymeric esters of unsaturated acids than for nitriles.

We claim:
1. A method of preparing a water insoluble biologically active product comprising subjecting a macroporous substantially hydrophobic polymeric carrier comprising a homopolymer or copolymer derived from (1) at least one acrylic monomer selected from the group consisting of alkylenediacrylates and dimethacrylates, oligo- and polyglycoldiacrylates and dimethacrylates, alkylenediacrylamides and methacrylamides, hydroxyalkylacrylates and methacrylates, oligo- and polyglycol monoacrylates and monomethacrylates, acrylonitrile and methacrylonitrile, or (2) a copolymer of at least one monomer of group (1) above with a vinyl monomer selected from the group consisting of vinylaniline, vinylpyridine and vinylcarbazol, to a superficial hydrolysis treatment with an aqueous alkaline medium to form free carboxylic acid groups in a thin surface layer of said polymeric carrier, subjecting the resulting superficially hydrolyzed polymeric carrier to an activation treatment comprising converting said free carboxylic acid groups to active carboxylic acid anhydride groups, and contacting the resulting activated polymeric carrier with a biologically active protein compound capable of being insolubilized and bound by reaction with said anhydride groups in said polymeric carrier.

2. A method as defined in claim 1 wherein said hydrolysis treatment is carried out at a temperature of 60°C. to 135°C. for 30 to 120 minutes.

3. A method as defined in claim 2 wherein said aqueous alkaline medium contains sodium hydroxide at a concentration of 2M to 10M.

4. A method as defined in claim 3 wherein said activation treatment comprises heating the superifically hydrolyzed polymeric carrier to a temperature of 200°C. to 250°C. for 30 to 300 minutes at a pressure of 0.2 to 0.01 Torr.

5. A method of preparing a water insoluble active product comprising subjecting a macroporous substantially hydrophobic polymeric carrier comprising a homopolymer or copolymer derived from (1) at least one acrylic monomer selected from the group consisting of alkylenediacrylates and dimethacrylates, oligo- and polyglycoldiacrylates and dimethacrylates, alkylenediacrylamides and methacrylamides, hydroxyalkylacrylates and methacrylates, oligo- and polyglycol monoacrylates and monomethacrylates, acrylonitrile and methacrylonitrile or (2) a copolymer of at least one monomer of group (1) above with a vinyl monomer selected from the group consisting of vinylaniline, vinylpyridine and vinylcarbazol, to a superficial hydrolysis treatment with an aqueous alkaline medium to form free carboxylic acid groups in a thin surface layer of said polymeric carrier, activating the resulting superficially thin layer of said hydrolyzed polymeric carrier by treating the superficially hydrolyzed polymeric carrier with a member of the group consisting of aceticanhydride and thionyl chloride to provide said surface layer with anhydride groups and contacting the resulting activated polymeric carrier with a biologically active protein compound capable of being insolubilized and bound by reaction with said anhydride groups in said polymeric carrier.

\* \* \* \* \*